United States Patent
Chua et al.

(10) Patent No.: US 8,891,240 B2
(45) Date of Patent: Nov. 18, 2014

(54) APPARATUS AND METHOD FOR COOLING A SEMICONDUCTOR DEVICE

(75) Inventors: Choon Meng Chua, Singapore (SG); Lian Ser Koh, Singapore (SG); Sze Wei Choong, Singapore (SG); Jacob Chee Hong Phang, Singapore (SG)

(73) Assignee: Semicaps Pte Ltd, Singapore (SG)

( * ) Notice: Subject to any disclaimer, the term of this patent is extended or adjusted under 35 U.S.C. 154(b) by 344 days.

(21) Appl. No.: 13/222,454

(22) Filed: Aug. 31, 2011

(65) Prior Publication Data

US 2012/0120599 A1 May 17, 2012

(51) Int. Cl.
*H05K 7/20* (2006.01)
*H01L 21/66* (2006.01)
*H01L 23/473* (2006.01)
*G01N 21/00* (2006.01)

(52) U.S. Cl.
CPC .......... *H01L 23/473* (2013.01); *H05K 7/20254* (2013.01); *H01L 22/30* (2013.01); *H05K 7/2049* (2013.01); *H05K 7/2039* (2013.01); *H05K 7/20436* (2013.01); *G01N 21/00* (2013.01); *H05K 7/20218* (2013.01); *H05K 7/20445* (2013.01); *H05K 7/20454* (2013.01)
USPC .......... 361/698; 361/689; 361/690; 361/699; 361/718; 361/719; 438/14; 438/16

(58) Field of Classification Search
CPC ...... H01L 23/473; H01L 22/30; G01N 21/00; H05K 7/2049; H05K 7/20445; H05K 7/20454; H05K 7/20436; H05K 7/20218; H05K 7/20254; H05K 7/2039
USPC ................ 361/689, 690, 698, 699, 718, 719; 438/14, 16
See application file for complete search history.

(56) References Cited

U.S. PATENT DOCUMENTS

| | | | |
|---|---|---|---|
| 4,193,445 A * | 3/1980 | Chu et al. | 165/79 |
| 4,226,281 A * | 10/1980 | Chu | 165/80.2 |
| 4,233,645 A * | 11/1980 | Balderes et al. | 361/698 |
| 4,235,283 A * | 11/1980 | Gupta | 165/80.4 |
| 4,381,032 A * | 4/1983 | Cutchaw | 165/46 |
| 4,639,829 A * | 1/1987 | Ostergren et al. | 361/718 |
| 4,685,211 A * | 8/1987 | Hagihara et al. | 29/832 |
| 4,693,303 A * | 9/1987 | Okada | 165/80.4 |
| 4,748,495 A * | 5/1988 | Kucharek | 257/713 |
| 5,023,695 A * | 6/1991 | Umezawa et al. | 257/714 |
| 5,097,385 A * | 3/1992 | Chao-Fan Chu et al. | 361/703 |
| 5,862,038 A * | 1/1999 | Suzuki et al. | 361/704 |
| 7,849,914 B2 * | 12/2010 | Di Stefano et al. | 165/46 |
| 8,472,188 B2 * | 6/2013 | Horiuchi et al. | 361/699 |
| 2006/0108097 A1 * | 5/2006 | Hodes et al. | 165/80.4 |
| 2007/0256810 A1 * | 11/2007 | Di Stefano et al. | 165/46 |

FOREIGN PATENT DOCUMENTS

DE    4124289 A1 *   1/1993    .............. H01L 23/46

* cited by examiner

*Primary Examiner* — Anatoly Vortman
(74) *Attorney, Agent, or Firm* — Volpe and Koenig, P.C.

(57) ABSTRACT

An apparatus and method for cooling a semiconductor device. The apparatus comprises a chamber configured for receiving a cooling fluid; and a plurality of contact elements comprising respective first ends disposed within the chamber; wherein, during operation, respective second ends of contact elements contact a surface of the semiconductor device for transferring heat generated in the semiconductor device to the cooling fluid.

16 Claims, 9 Drawing Sheets

SECTION A-A (a)

(b)

(c)

APPARATUS AND METHOD FOR COOLING A SEMICONDUCTOR DEVICE

FIELD OF INVENTION

The present invention relates broadly to an apparatus and method for cooling a semiconductor device.

BACKGROUND

During electrical testing of a semiconductor device, an electric current may be supplied to relevant components of the semiconductor device under test. With increasing metal layers and flip chip bonding, analysis of the integrated circuits (IC) on the semiconductor device can typically only be done from the backside of the chip through the silicon substrate using infrared imaging. It has been noted that the semiconductor device may heat up during such testing due to power dissipation and may need to be cooled.

In one existing cooling method, a cooled diamond window is used to press on the backside of the semiconductor device. This method allows air-gap lens operation. The diamond window allows the system to perform the analysis through the silicon substrate while testing. The diamond conducts heat from the semiconductor device to an attached copper heat exchanger block. Typically, the heat exchanger uses a cooled liquid or super cooled air. Another version of this method involves having a small opening on the diamond window to allow a Solid Immersion Lens (SIL), which can enhance the imaging resolution, to land on the device.

However, in the above method, the thermal resistance is high between the cold contact (diamond window) and the semiconductor device, and between the cold contact and the heat exchanger block, making it difficult for the user to operate the device at a higher power. In addition, in the above method, device planarity requirements are typically stringent, and passive components protruding from the device may have to be removed.

In another existing cooling method, a liquid jet is used to spray a cooled liquid onto the silicon substrate of the semiconductor device. The sprayed liquid is then collected back to the heat exchanger. However, this method typically can only be used with an SIL which has sealed optics. Also, this method can only cool the device to temperatures above 10 degrees Celsius (° C.).

A need therefore exists to provide an apparatus and method for cooling a semiconductor device that seek to address at least some of the above problems.

SUMMARY

In accordance with a first aspect of the present invention, there is provided an apparatus for cooling a semiconductor device, comprising:
  a chamber configured for receiving a cooling fluid; and
  a plurality of contact elements comprising respective first ends disposed within the chamber;
  wherein, during operation, respective second ends of contact elements contact a surface of the semiconductor device for transferring heat generated in the semiconductor device to the cooling fluid.

The contact elements may be independently adjustable.

The contact elements may be mounted to the chamber in a spring-loaded type configuration.

Each of the contact elements may be anchored on a respective elastic O-ring.

The contact elements may be fabricated from a heat conducting material.

The contact elements each may comprise a first bulk material coated, at a contact area of the contact element, with a second material.

The first bulk material may comprise copper and the second material may comprise gold.

The chamber may further comprise an inlet and an outlet for forming a continuous flow of the cooling fluid.

The first ends of the contact elements may be formed integrally with or be attached to respective cooling fins.

The chamber may be configured to allow inspection of the silicon substrate by at least one of a solid immersion lens (SIL) and an air gap lens.

In accordance with a second aspect of the present invention, there is provided a system for inspecting and testing a semiconductor device, the system comprising the cooling apparatus as defined in the first aspect.

In accordance with a third aspect of the present invention, there is provided a method for cooling a semiconductor device, the method comprising the steps of:
  providing a cooling fluid in a chamber;
  providing a plurality of contact elements comprising respective first ends disposed within the chamber; and
  coupling respective second ends of the contact elements to a surface of the semiconductor device for transferring heat generated in the semiconductor device to the cooling fluid.

The cooling fluid may comprise a cooling gas or a cooling liquid.

The cooling gas may comprise super-cooled air.

The cooling liquid may comprise water or diluted glycol.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

Figure 1A:
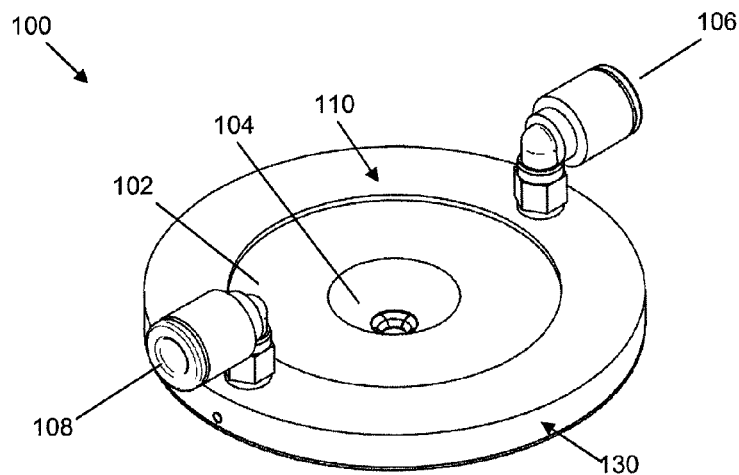
FIG. 1(a) shows a perspective view of a cooling apparatus according to an example embodiment.
Figure 1B:
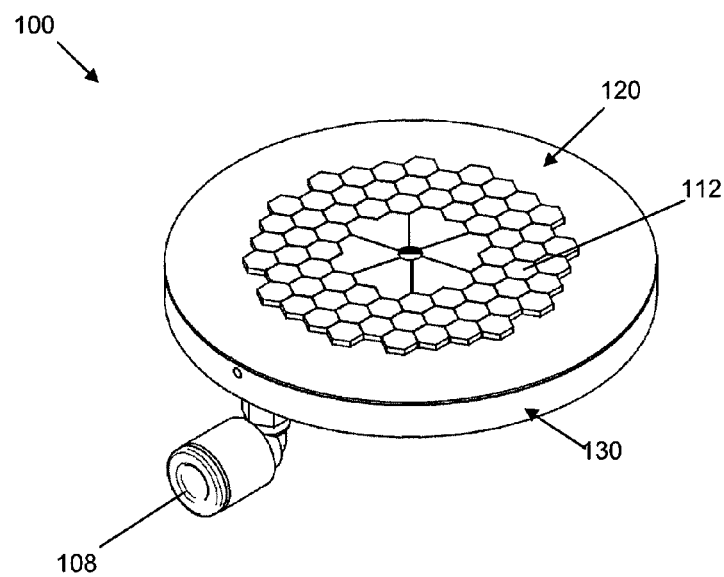
FIG. 1(b) shows an alternative perspective view of the cooling apparatus of FIG. 1(a).
Figure 1C:
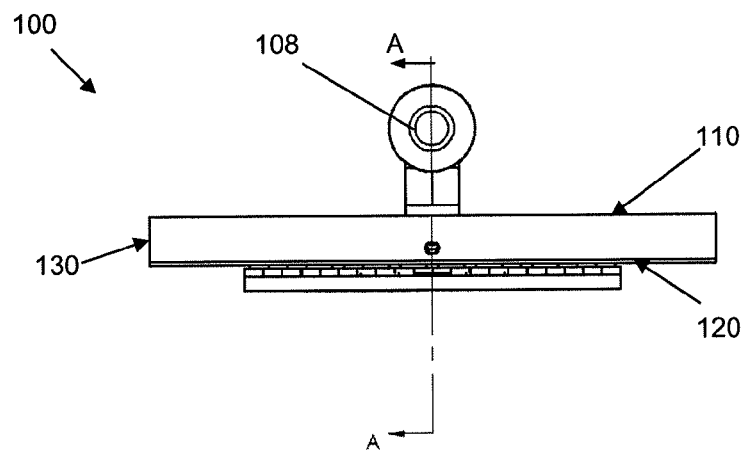
FIG. 1(c) shows a side view of the cooling apparatus of FIG. 1(a).
Figure 1D:
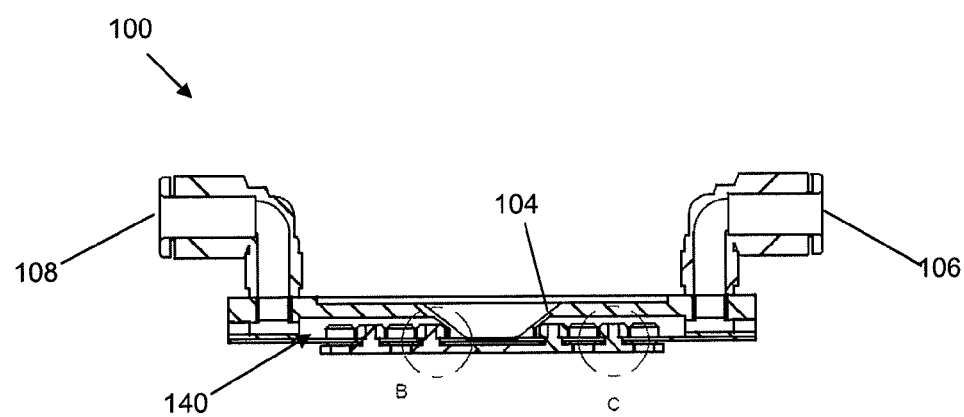
FIG. 1(d) shows a cross-sectional view of the cooling apparatus about a line A-A in FIG. 1(c) according to an example embodiment.

FIG. 1(a) shows a perspective view of a cooling apparatus 100 according to an example embodiment. FIG. 1(b) shows an alternative perspective view of the cooling apparatus 100 of FIG. 1(a). FIG. 1(c) shows a side view of the cooling apparatus 100 of FIG. 1(a). FIG. 1(d) shows a cross-sectional view of the cooling apparatus 100 about a line A-A in FIG. 1(c) according to an example embodiment.

In the example embodiment, the cooling apparatus 100 is in the form of a circular disc comprising an upper face 110 and a lower face 120. The upper face 110 of the cooling apparatus 100 is configured to receive a Solid Immersion Lens (SIL) (not shown). For example, as can be seen from FIG. 1(a), a recess 102 comprising a substantially conical aperture 104 is formed on the upper face 110 such that, during testing operation, the conical aperture 104 accommodates a corresponding conical portion of the SIL. In an alternate embodiment using an air-gap lens, the air-gap lens may also be positioned directly above the conical aperture 104.

As can be seen from FIG. 1(d), the upper face 110, the lower face 120 and a rim 130 of the cooling apparatus 100 together define a hollow chamber 140 capable of containing a cooling fluid (gas or liquid). In the example embodiment, an inlet 106 is provided on the top face 110 for injecting the cooling fluid (gas or liquid), e.g. super-cooled air, water or diluted glycol, into the chamber 140, and an outlet 108 is provided on the top face 110 diametrically opposite the inlet 106 for removing said fluid from the chamber 140 during the cooling process, which will be described in detail below. The inlet 106 and outlet 108 thus enable a continuous flow of cooling fluid in the example embodiment.

In addition, as can be seen from FIG. 1(b), an array of contact elements 112 (herein interchangeably referred to as contacts 112) are mounted adjacent the lower face 120. In the example embodiment, the contact elements 112 are adjustable independently of one another, thus enabling a better surface contact with the target semiconductor device, such as a die, without requiring a high degree of planarity. Preferably, the contact elements 112 are fabricated using a heat conducting material. In FIG. 1(b) the contact area of some of the contact elements 112 are shown as hexagons. However, it should be appreciated that other shapes, e.g. triangle, square or polygon, may be used in alternate embodiments.

Figure 2:
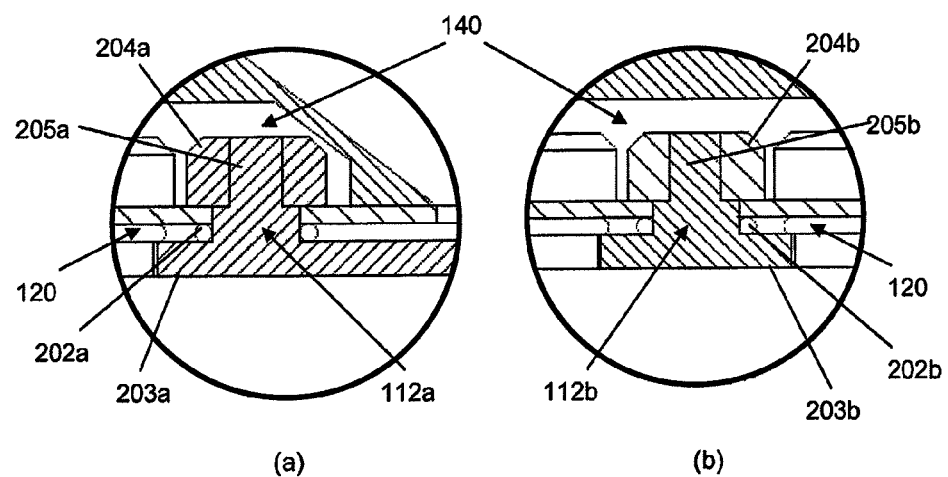
FIG. 2(a) shows an enlarged view of detail B in FIG. 1(d).
FIG. 2(b) shows an enlarged view of detail C in FIG. 1(d).

Also, can be seen in FIGS. 1(b) and 1(d), the contacts 112 in the central region of the lower face 120 have respective contact areas configured for maximizing contact with the semiconductor device without covering the aperture 104 where the SIL lands, and for accommodating the limited mounting space adjacent to the conical aperture 104 in the chamber 140. In the example embodiment, this is achieved by using central contacts 112 with petal-shaped contact areas as shown in FIG. 1(b) and by positioning a mounting point of each central contact 112 nearer to the respective outer end where more space is available (as illustrated in detail in FIG. 2(a)). Preferably, this arrangement helps to achieve weight balance as the outer end is typically larger than the inner end.

FIG. 2(a) shows an enlarged view of detail B in FIG. 1(d). FIG. 2(b) shows an enlarged view of detail C in FIG. 1(d). In FIGS. 2(a)-(b), the same reference numerals are used to identify the same parts compared to FIGS. 1(a)-(d).

The contact elements 112a, 112b are preferably mounted in a spring-loaded type configuration. In the example embodiment, the spring-loaded type configuration comprises anchoring the contact elements 112a, 112b on respective O-rings 202a, 202b disposed between the lower face 120 and respective bottom portions 203a, 203b. In the example embodiment, the O-rings 202a, 202b are fabricated from an elastic material such as rubber or silicone to provide spring loading for the contact elements 112a, 112b respectively. Thus, the array of contact elements 112a, 112b can advantageously conform to and maintain good contact even with a die surface that does not have a high degree of planarity. Also, the contact elements 112a, 112b, which are typically fabricated from a thermally conductive material such as copper, are coated with a relatively softer material such as gold at least on the contact areas of the respective bottom portions 203a, 203b in the example embodiment, for further enhancement of the thermal contact with the surface of the die.

Also, in the example embodiment, top portions 205a, 205b of the contact elements 112a, 112b are disposed within the chamber 140 such that, during operation, heat is conducted from the silicon substrate to the contact elements 112a, 112b and is removed by direct contact with the cooling fluid, e.g. super-cooled air, water or diluted glycol, present in the chamber 140. The contact elements 112a, 112b thus increase the effective cooling surface of the silicon substrate during operation. In a preferred embodiment, the top portions 205a, 205b of the contact elements 112a, 112b are formed integrally with or are secured to respective cooling fins 204a, 204b, which are also made of a heat conducting material, to enhance the heat exchange with the cooling fluid in the chamber 140.

Figure 3:
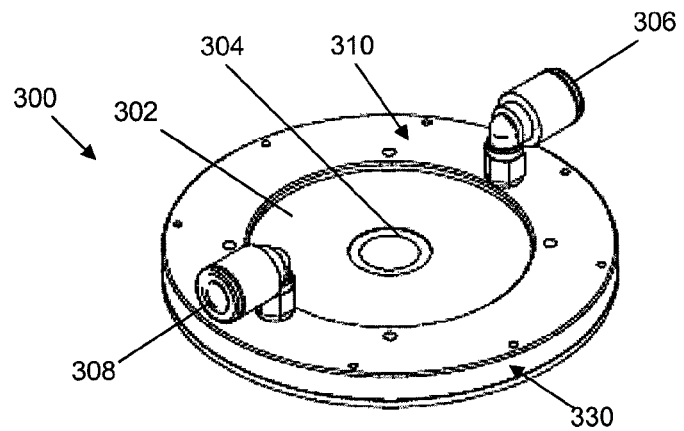
FIG. 3(a) shows a perspective view of a cooling apparatus according to an alternate embodiment.
FIG. 3(b) shows an alternative perspective view of the cooling apparatus of FIG. 3(a).
FIG. 3(c) shows a side view of the cooling apparatus of FIG. 3(a).
Figure 3:
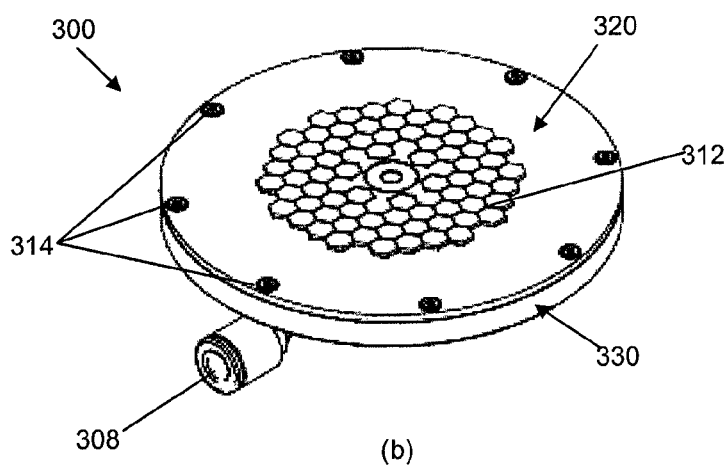
Figure 3:
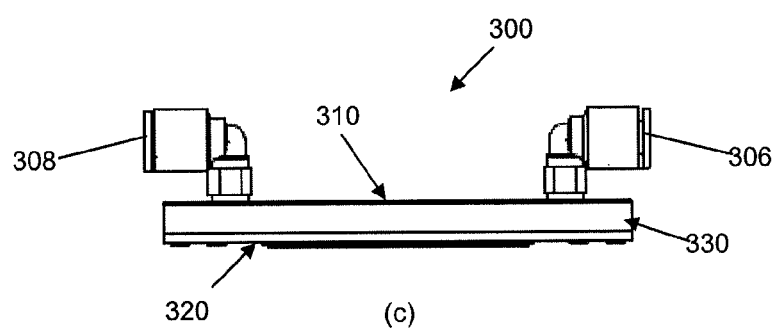

FIG. 3(a) shows a perspective view of a cooling apparatus 300 according to an alternate embodiment. FIG. 3(b) shows an alternative perspective view of the cooling apparatus 300 of FIG. 3(a). FIG. 3(c) shows a side view of the cooling apparatus 300 of FIG. 3(a).

Similar to the cooling apparatus 100 described above with respect to FIG. 1, the cooling apparatus 300 in this embodiment is in the form of a circular disc comprising an upper face 310, a rim 330 and a lower face 320. Fastening means, e.g. screws 314, are used to secure the upper face 310 to the lower face 320. The upper face 310 of the cooling apparatus 300 is configured to receive a Solid Immersion Lens (SIL) (not shown), e.g. by having a recess 302 comprising a substantially conical aperture 304 formed on the upper face 310. During testing operation, the conical aperture 304 can accommodate a corresponding conical portion of the SIL. In another embodiment using an air-gap lens, the air-gap lens may also be positioned directly above the conical aperture 304. Also, an inlet 306 is provided for injecting the cooling fluid (gas or liquid), e.g. super-cooled air, water or diluted glycol, into a chamber (not shown in FIG. 1). The fluid that has been used for cooling is then removed via an outlet 108 disposed diametrically opposite the inlet 106, such that the inlet 106 and outlet 108 enable a continuous flow of the cooling fluid across the chamber in the example embodiment.

Further, an array of contact elements 312 (herein interchangeably referred to as contacts 312) are mounted adjacent the lower face 320. In the example embodiment, the contact elements 312 are adjustable independently of one another, thus enabling a better surface contact with the target semiconductor device, for example a die, without requiring a high degree of planarity. Preferably, the contact elements 312 are fabricated using a thermally conductive material such as copper, and may be coated with a relatively softer material such as gold at least on the contact areas for further enhancement of the thermal contact with the die. In FIG. 3(b) the contact area of some of the contact elements 312 are shown as hexagons. However, it should be appreciated that other shapes, e.g. triangle, square or polygon, may be used in other embodiments.

FIG. 4(a) shows a cross-sectional view of the cooling apparatus 300 of FIG. 3(a) according to an example embodiment. As can be seen from FIG. 4(a), the upper face 310, the lower face 320 and a rim 330 of the cooling apparatus 300 together define a hollow chamber 340 for containing the cooling fluid, as described above. Preferably, the degree of slant of the conical aperture 304 is adjustable, depending on e.g. the type of lens used. For example, the conical aperture 304 shown in FIG. 4(a) is more pointed compared to that shown in FIG. 2.

FIG. 4(b) shows an enlarged view of a center contact 410 in detail B of FIG. 4(a). FIG. 4(c) shows an enlarged view of contact elements 312 in detail C of FIG. 4(a). As shown in FIG. 4(b), the center contact 410 comprises a hollow center portion defining the conical aperture 304 (FIG. 3(a)), recesses (to be shown in FIG. 5) to receive elastic O-rings 404, 406. The elastic O-rings 404, 406 provide tight fluid seals between the center contact 410 and an upper plate 412 and lower plate 402 respectively such that the cooling fluid may not leak from the chamber 340.

Referring now to FIG. 4(c), the contact elements 312a, 312b, 312c are arranged such that their respective bottom portions are in contact with one another, while gaps exist between their respective top portions to allow the cooling fluid to circulate within the chamber 340. In the example embodiment, the top portion of each contact element 312a, 312b, 312c is substantially cylindrical and configured to have a biasing element, here in the form of a spring 418a, 418b, 418c to be mounted thereon. Each of the springs 418a, 418b, 418c is biased against the top plate 412 at one end, and against the bottom plate 402 at another end. This arrangement allows contact elements 312a, 312b, 312c to be mounted in a spring-loaded type configuration in the example embodiment, such that the contact elements 312a, 312b, 312c are adjustable during operation. Further, each contact element (e.g. 312b) comprises a recess for receiving a respective O-ring 414b for establishing a fluid seal with the bottom plate 402 such that the cooling fluid may not leak from the chamber 340.

Figure 4:
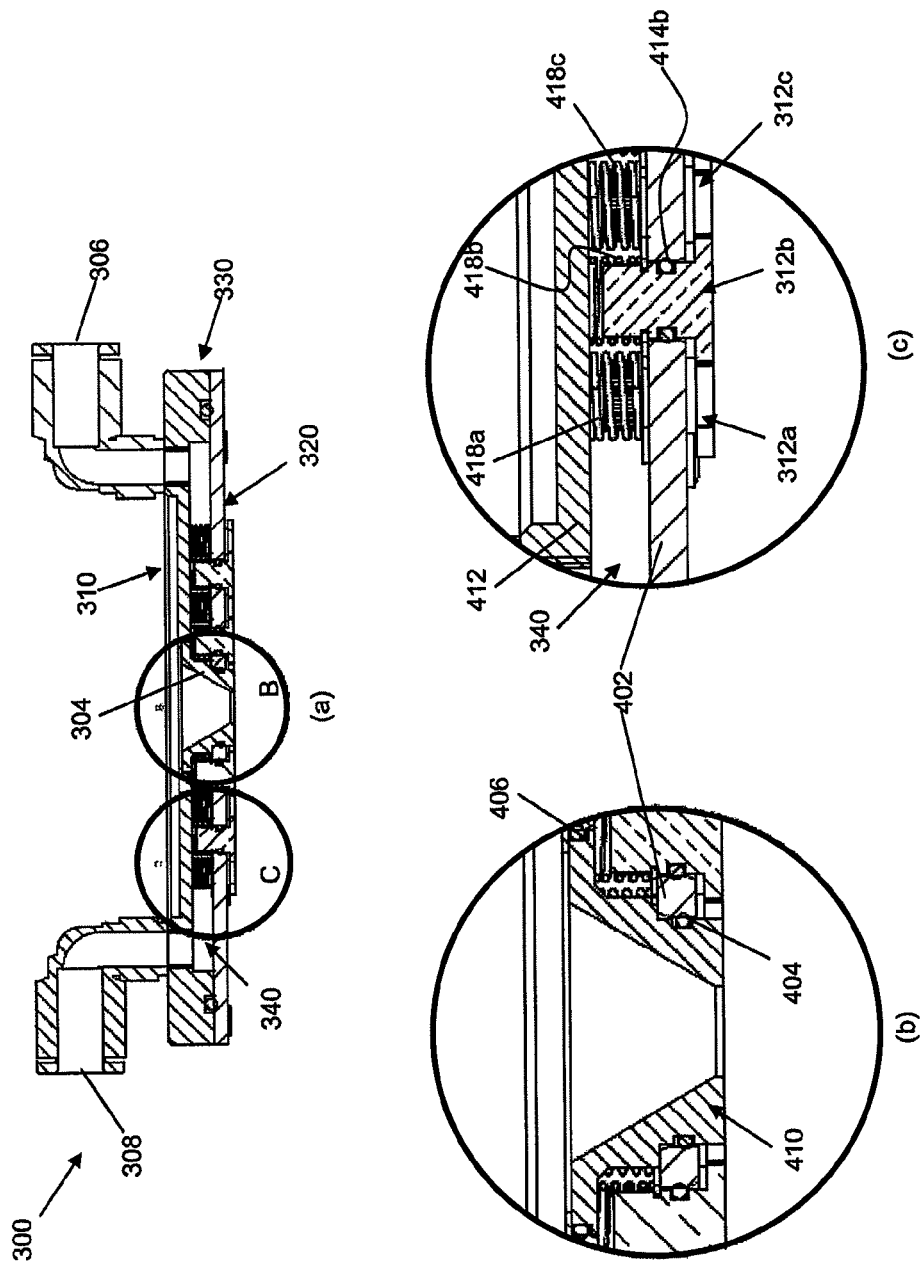
FIG. 4(a) shows a cross-sectional view of the cooling apparatus of FIG. 3(a) according to an example embodiment.
FIG. 4(b) shows an enlarged view of a center contact in detail B of FIG. 4(a).
FIG. 4(c) shows an enlarged view of contact elements in detail C of FIG. 4(a).
Figure 5:
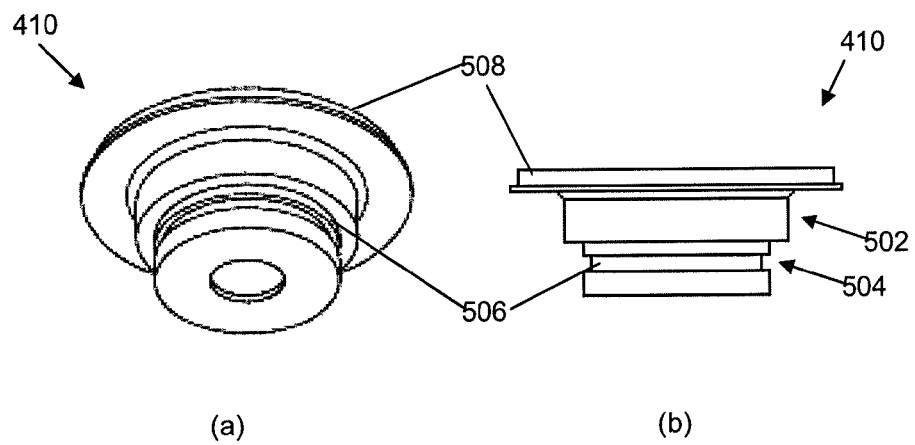
FIG. 5(a) shows a perspective view of the center contact of FIG. 4(b) according to an example embodiment.
FIG. 5(b) shows a side view of the center contact of FIG. 5(a).

As shown in FIG. 4, each of the center contact 410 and contact elements 312 in the example embodiment is mounted by the respective spring and O-ring, allowing them to be adjustable independently of one another. Thus, in the example embodiment, the array of contact elements 312a, 312b, 312c can advantageously conform to and maintain good contact even with a die surface that does not have a high degree of planarity.

FIG. 5(a) shows a perspective view of the center contact 410 of FIG. 4(b) according to an example embodiment. FIG. 5(b) shows a side view of the center contact 410 of FIG. 5(a). The center contact 410 comprises an upper cylindrical portion 502 where the spring 408 (FIG. 4(b)) is mounted on, and a lower cylindrical portion 504 comprising a smaller diameter than the upper cylindrical portion 502 for mounting to the lower plate 402 (FIG. 4(b)). A recess 508 is disposed on a top rim of the center contact 410 for receiving the O-ring 406 (FIG. 4(b)), while a recess 506 is disposed on the lower cylindrical portion 504 for receiving the O-ring 404 (FIG. 4(b)).

Figure 6:
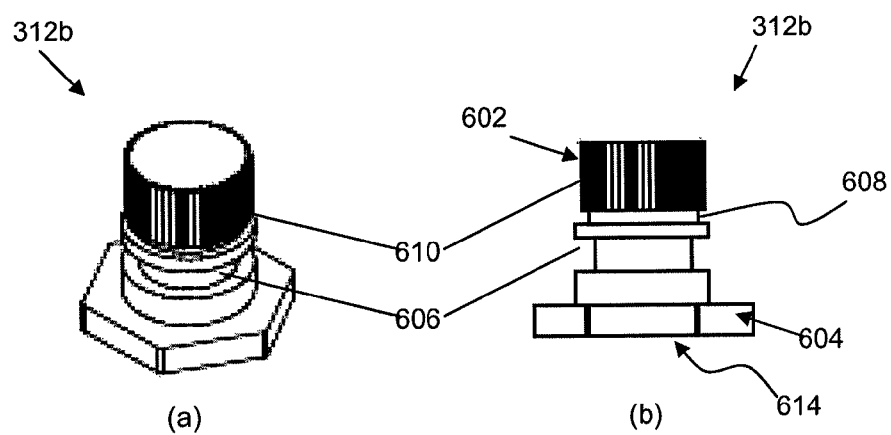
FIG. 6(a) shows a perspective view of the contact element of FIG. 4(c) according to an example embodiment.
FIG. 6(b) shows a side view of the contact element of FIG. 6(a).

FIG. 6(a) shows a perspective view of the contact element 312b of FIG. 4(c) according to an example embodiment. FIG. 6(b) shows a side view of the contact element 312b of FIG. 6(a). The contact element 312b comprises a cylindrical upper portion 602 where the spring 418 (FIG. 4(c)) is mounted on, and a lower portion 604 defining e.g. a hexagonal contact surface 614. Additionally, the contact element 312b comprises a recess 606 for receiving the O-ring 414b (FIG. 4(c)), and a recess 608 for receiving, e.g. a clip to hold the contact element 312b in a normal position. During operation, the contact surface 614 contacts the semiconductor device (not shown) and transfers the heat from the semiconductor device to the upper portion 602, where the heat is removed by the cooling fluid. In a preferred embodiment, the upper portion 602 comprises vertical grooves 610 for increasing a surface area in contact with the cooling fluid, thereby enhancing the heat transfer from the contact element 312b to the cooling fluid.

Figure 7:
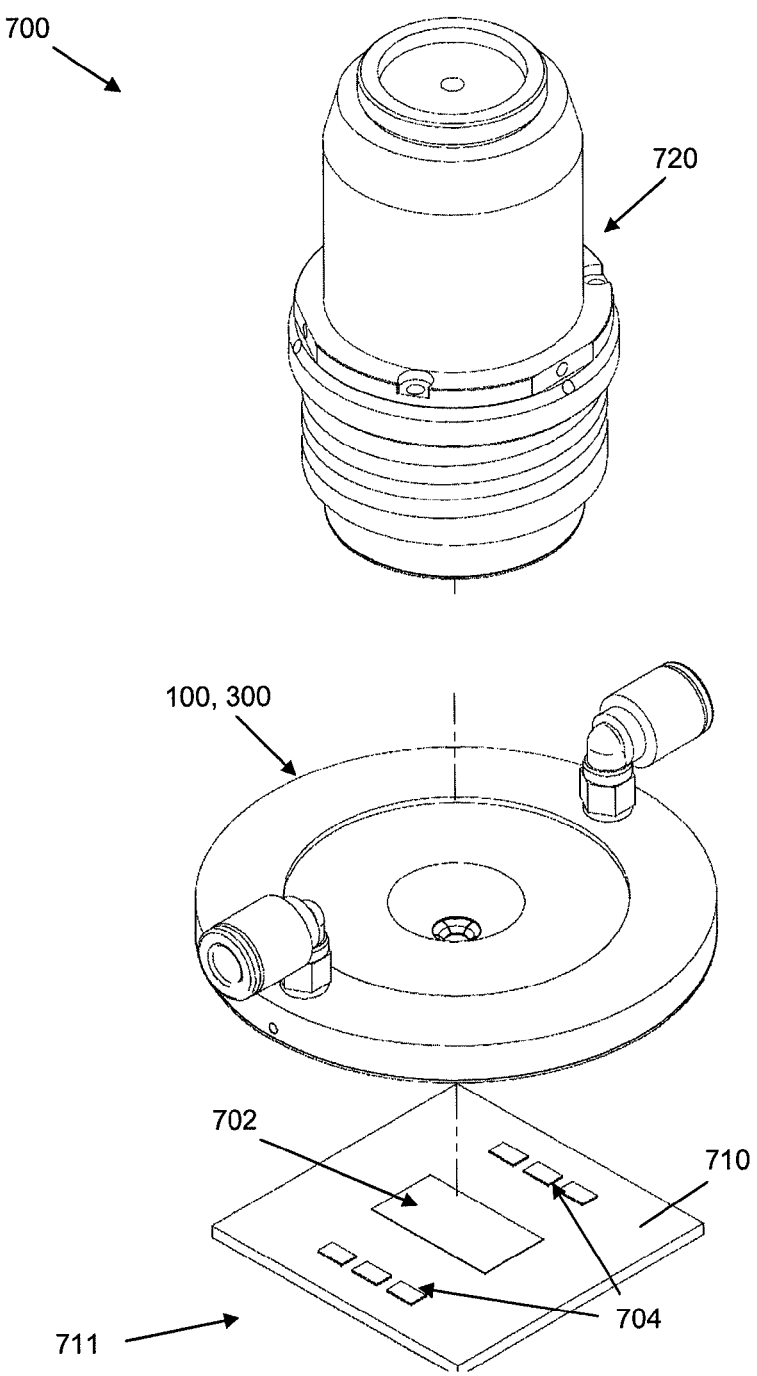
FIG. 7 shows an exploded perspective view of a system for inspecting a semiconductor device according to an example embodiment.

FIG. 7 shows an exploded perspective view of a system 700 for inspecting a packaged semiconductor device 711 such as a microprocessor packaged with flip chip technology, according to an example embodiment. The die 702 is typically inverted and provided on a package substrate 710 together with die-side components 704, as will be appreciated by a person skilled in the art. The packaged semiconductor device 711 is usually mounted in a socket (not shown) during testing. The cooling apparatus 100, 300 is disposed between a solid immersion lens (SIL) assembly 720 and the packaged semiconductor device 711 such that the upper face of the cooling apparatus 100, 300 is adjacent to the SIL assembly 720, while the lower face of the cooling apparatus 100, 300 is adjacent to the backside of the die 702 in the example embodiment. Thus, the cooling apparatus 100, 300 advantageously allows inspection and analysis of the die 702 through the silicon substrate (or backside) while removing heat generated by the die 702.

Figure 8:
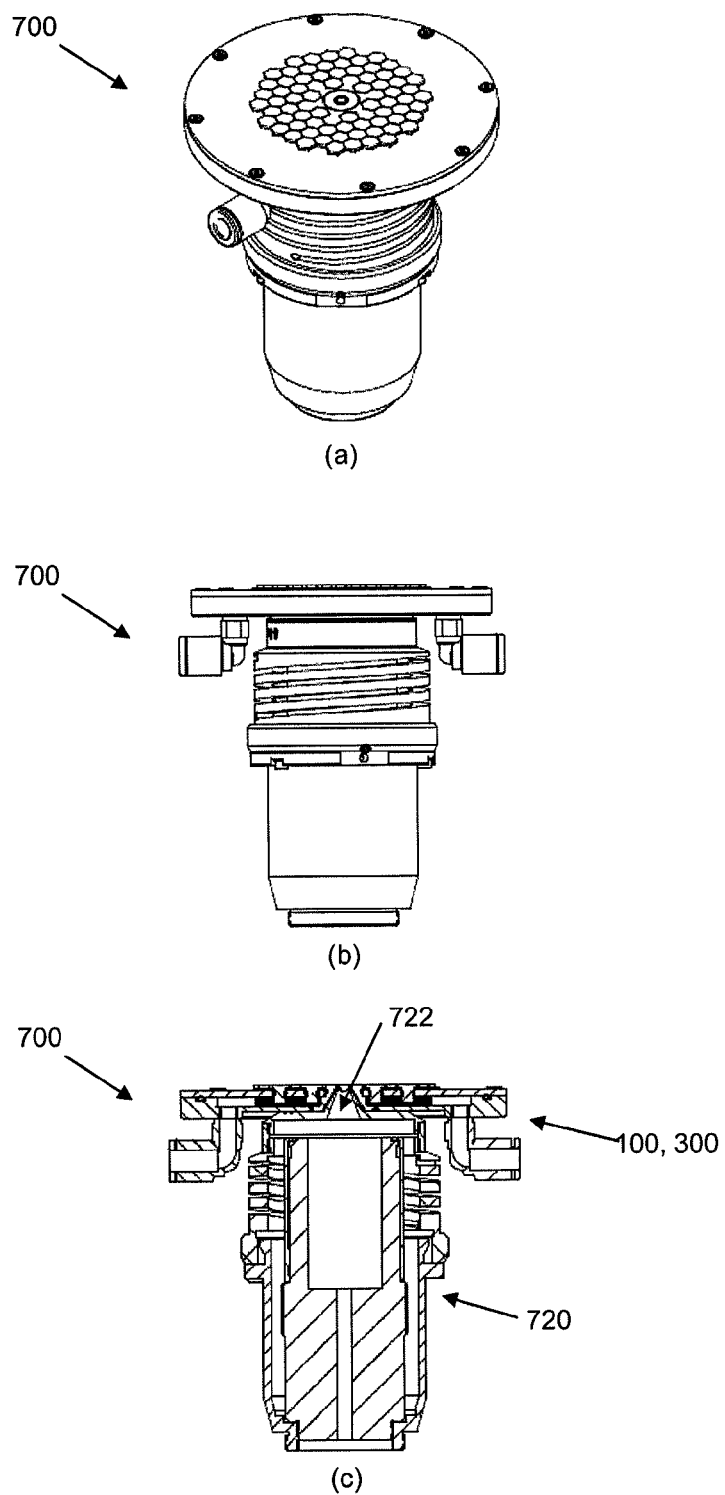
FIG. 8(a) shows a perspective view of the system of FIG. 7 when the SIL assembly is in contact with the cooling apparatus.
FIG. 8(b) shows a side view of the system of FIG. 8(a).
FIG. 8(c) shows a cross-sectional view of the system of FIG. 8(a).

FIG. 8(a) shows a perspective view of the system 700 of FIG. 7 when the SIL assembly 720 is in contact with the cooling apparatus 100, 300. FIG. 8(b) shows a side view of the system 700 of FIG. 8(a). FIG. 8(c) shows a cross-sectional view of the system 700 of FIG. 8(a). As can be seen in e.g. FIG. 8(c), the conical aperture 104 of the cooling apparatus 100, 300 receives a conical tip 722 of the SIL assembly 720, e.g. during operation, for inspection of the packaged semiconductor device (not shown).

As described above, the cooling apparatus in the example embodiments has advantageously provided improved thermal contact and conductivity such that the thermal resistance is advantageously reduced, thereby allowing the user to operate the semiconductor device at a higher power. Preferably, the cooling apparatus in the example embodiments can cool the semiconductor device to temperatures below 0° C. and does not require the surface of the silicon substrate to have high planarity. For example, the die may be polished prior to testing to remove at least part of the silicon substrate, and planarity requirements for such polishing can preferably be relaxed. Furthermore, after polishing, the surface of the die is usually lower than the die-side components on the packaged semiconductor device. The cooling apparatus can accommodate the now taller die-side components and the die-side components, advantageously, do not need to be removed in the example embodiments. Also, since the cooling fluid is contained within the cooling apparatus rather than being sprayed onto the semiconductor device, the SIL advantageously does not need to have sealed optics in the example embodiments.

Figure 9:
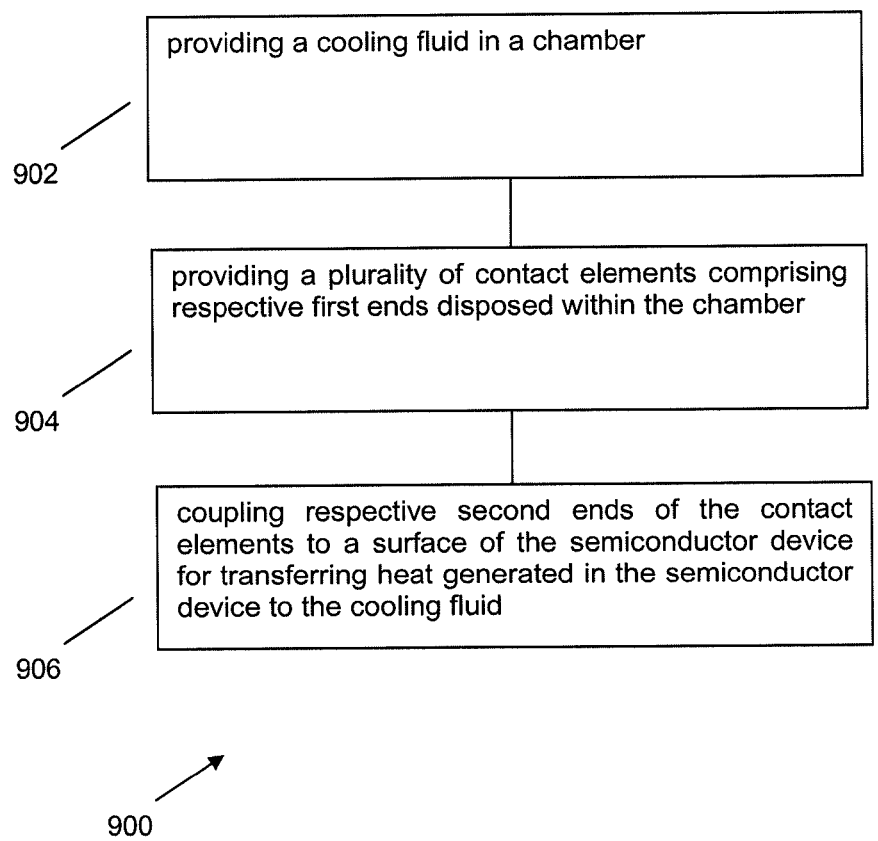
FIG. 9 shows a flow chart illustrating a method for cooling a semiconductor device according to an example embodiment.

FIG. 9 shows a flow chart 900 illustrating a method for cooling a semiconductor device according to an example embodiment. At step 902, a cooling fluid is provided in a chamber. At step 904, a plurality of contact elements comprising respective first ends disposed within the chamber are provided. At step 906, respective second ends of the contact elements are coupled to a surface of the semiconductor device for transferring heat generated in the semiconductor device to the cooling fluid.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

The invention claimed is:

1. An apparatus for cooling a semiconductor device, comprising:
    a chamber configured for receiving a cooling fluid, the chamber defined by an upper face, a lower face and a rim of the apparatus; and
    a plurality of contact elements comprising respective first ends disposed within the chamber and respective second ends extending and protruding through the lower face;
    wherein, during operation, the respective second ends of the contact elements contact a surface of the semiconductor device for transferring heat generated in the semiconductor device to the cooling fluid; and
    a through opening formed in the apparatus and extending through the upper face and the lower face for allowing inspection of the semiconductor device by at least one of a solid immersion lens (SIL) and an air gap lens.

2. The apparatus as claimed in claim 1, wherein the contact elements are independently adjustable.

3. The apparatus as claimed in claim 2, wherein the contact elements are mounted to the chamber in a spring-loaded type configuration.

4. The apparatus as claimed in claim 3, wherein each of the contact elements is anchored on a respective elastic O-ring.

5. The apparatus as claimed in claim 3, wherein a spring is mounted on a respective first end of each of the contact elements.

6. The apparatus as claimed in claim 1, wherein the contact elements are fabricated from a heat conducting material.

7. The apparatus as claimed in claim 6, wherein the contact elements each comprises a first bulk material coated, at a contact area of the contact element, with a second material.

8. The apparatus as claimed in claim 7, wherein the first bulk material comprises copper and the second material comprises gold.

9. The apparatus as claimed in claim 1, wherein the chamber further comprises an inlet and an outlet for forming a continuous flow of the cooling fluid.

10. The apparatus as claimed in claim 1, wherein the first ends of the contact elements are formed integrally with or are attached to respective cooling fins.

11. The apparatus as claimed in claim 1, wherein the first ends of the contact elements each comprises vertical grooves.

12. A system for inspecting and testing a semiconductor device, the system comprising the cooling apparatus as claimed in claim 1.

13. A method for cooling a semiconductor device, the method comprising the steps of:
    providing a cooling fluid in a chamber, the chamber being defined by an upper face, a lower face and a rim of a cooling apparatus;
    providing a plurality of contact elements comprising respective first ends disposed within the chamber and respective second ends extending and protruding through the lower face;
    coupling the respective second ends of the contact elements to a surface of the semiconductor device for transferring heat generated in the semiconductor device to the cooling fluid; and
    inspecting the semiconductor device by at least one of a solid immersion lens (SIL) and an air gap lens using a through opening formed in the apparatus and extending through the upper face and the lower face.

14. The method as claimed in claim 13, wherein the cooling fluid comprises a cooling gas or a cooling liquid.

15. The method as claimed in claim 14, wherein the cooling gas comprises super-cooled air.

16. The method as claimed in claim 14, wherein the cooling liquid comprises water or diluted glycol.

* * * * *